United States Patent [19]
Okabe et al.

[11] Patent Number: 5,894,021
[45] Date of Patent: *Apr. 13, 1999

[54] IONTOPHORETIC TRANSDERMAL DRUG-DELIVERY INTERFACE AND SKIN TREATMENT AGENT AND TREATMENT METHOD USING THE SAME

[75] Inventors: Keiichiro Okabe, Tokyo; Shinichi Sunahori, Sagamihara; Emi Kyo, Kawasaki, all of Japan

[73] Assignee: Kabushiki Kaisya Advance, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/649,583
[22] PCT Filed: Sep. 29, 1995
[86] PCT No.: PCT/JP95/02000
  § 371 Date: May 23, 1996
  § 102(e) Date: May 23, 1996
[87] PCT Pub. No.: WO96/10439
  PCT Pub. Date: Apr. 11, 1996

[30] Foreign Application Priority Data

Sep. 30, 1994 [JP] Japan ................................ 6-259677
Dec. 15, 1994 [JP] Japan ................................ 6-332806

[51] Int. Cl.$^6$ ............................... A61F 13/00; A61K 9/70
[52] U.S. Cl. .................................... 424/449; 604/20
[58] Field of Search ........................ 424/449; 604/20; 128/639, 640, 644

[56] References Cited

U.S. PATENT DOCUMENTS 5,224,927  7/1993  Tapper ........................... 604/20

FOREIGN PATENT DOCUMENTS

| 61221125 | of 0000 | Japan . |
| 63-57527 | 3/1988 | Japan . |
| 2-274260 | 11/1990 | Japan . |
| 3-12173 | 1/1991 | Japan . |
| 5-33738 | 5/1993 | Japan . |
| 6-16535 | 1/1994 | Japan . |

OTHER PUBLICATIONS

Journal of Controlled Release 18, (1992) pp. 213–220. S. Kumar et al., "In vivo transdermal iontophoretic delivery of growth hormone releasing factor GRF (1–44) in hairless guines pigs."
J. Controlled Release 18, 213–220, 1992.

*Primary Examiner*—Thurman K. Page
*Assistant Examiner*—Kathryne E. Shelborne
*Attorney, Agent, or Firm*—Christie, Parker & Hale, LLP

[57] ABSTRACT

An iontophoretic interface comprising a non-electroconductive material of a porous or capillary structure, coated and treated with a disinfecting and preserving ionic surfactant on the portion of the surface coming into contact with the drug as well as a skin pre-treatment composition and a skin pre-treatment method.

12 Claims, 3 Drawing Sheets

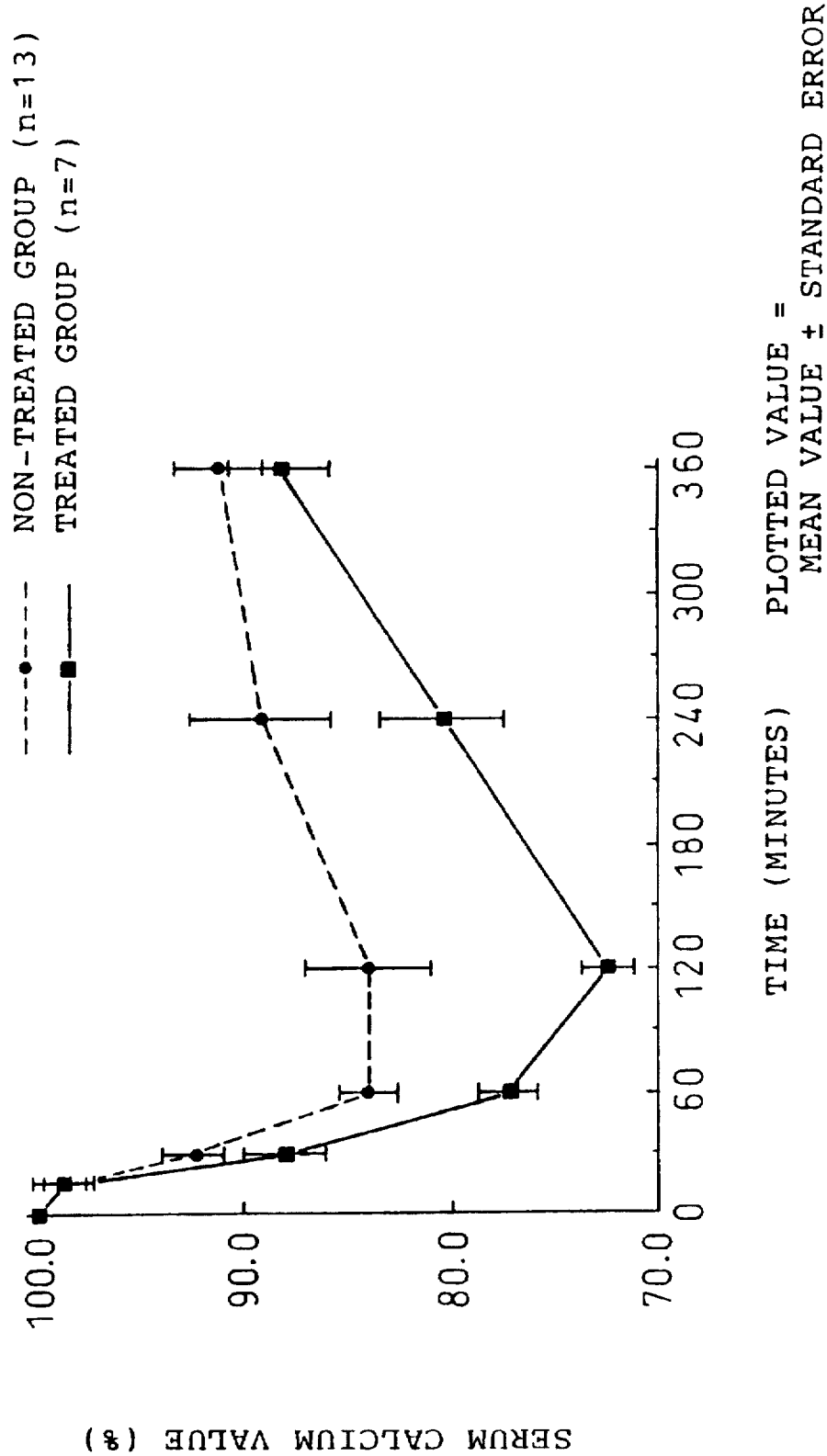

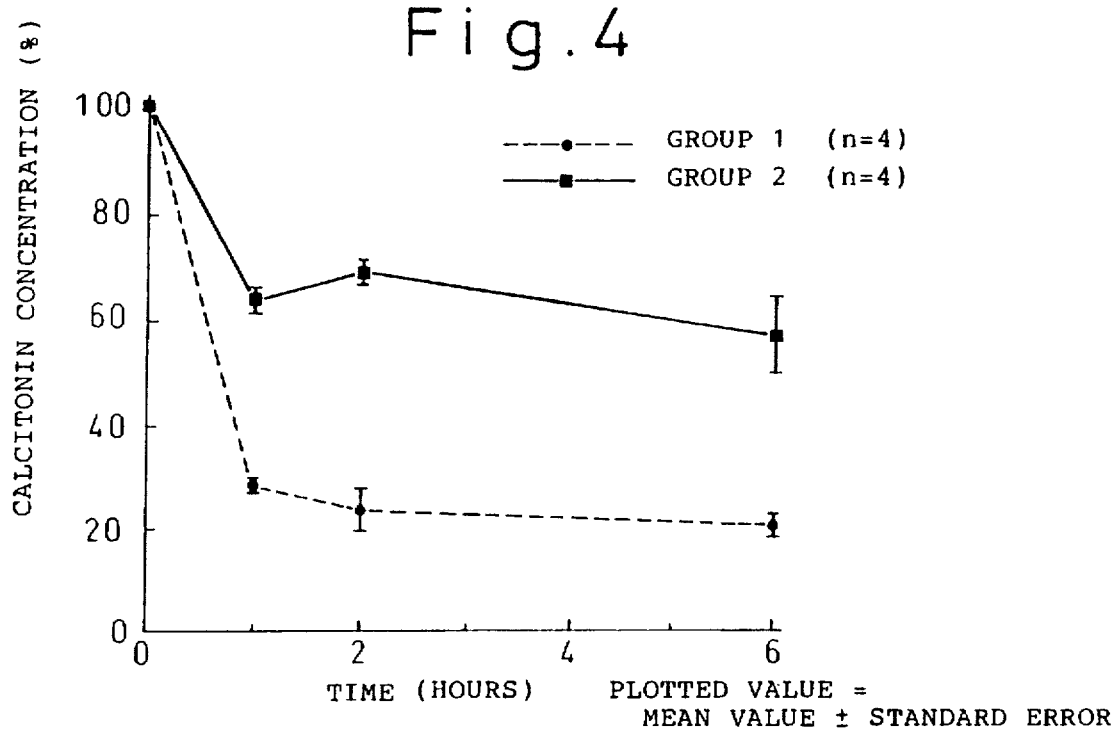
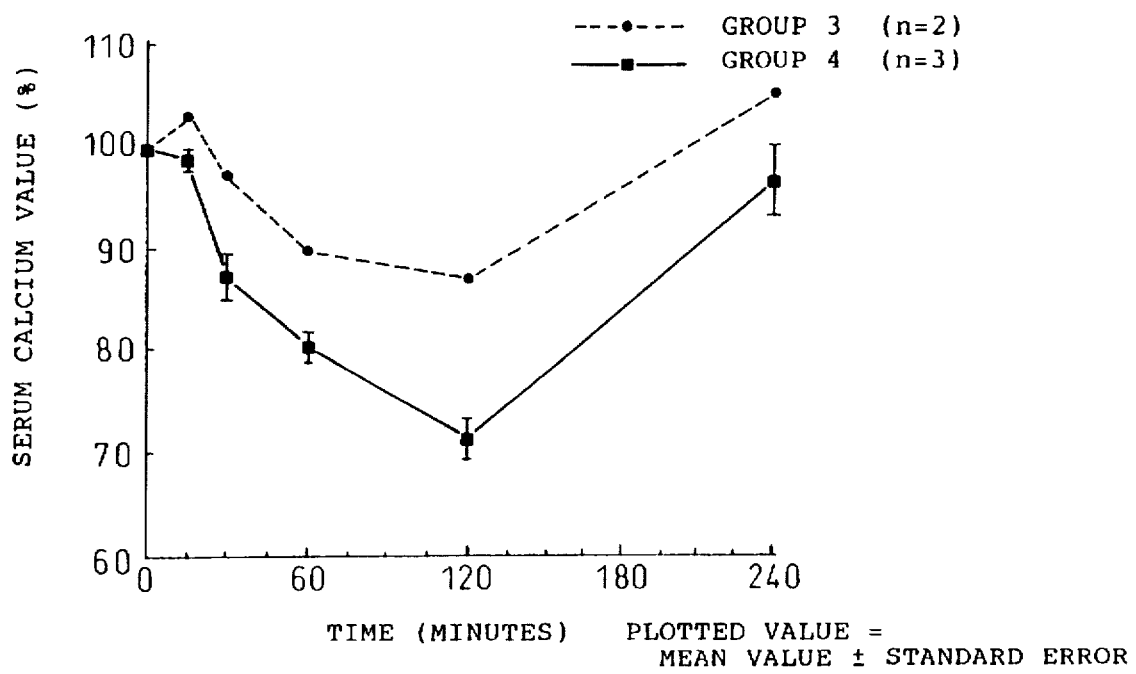

IONTOPHORETIC TRANSDERMAL DRUG-DELIVERY INTERFACE AND SKIN TREATMENT AGENT AND TREATMENT METHOD USING THE SAME

This application is a 371 of PCT/JP95/02000 filed Sep. 29, 1995.

TECHNICAL FIELD

The present invention relates to an iontophoretic interface for electrically permeating of a drug through the skin. More particularly, it relates to an iontophoretic interface suitable for effectively causing absorption into the skin of an ionic bioactive peptide-type drug having a high activity in a minute amount.

The present invention further relates to a skin treatment composition used mainly for pretreatment at the time of iontophoretic transdermal drug delivery and a pretreatment method using the same. More particularly, it relates to a skin treatment agent capable of effectively absorbing, into the skin, an ionic bioactive peptide-type drug having a high activity in a minute amount when using iontophoresis for electrically absorbing a drug into the skin, in particular enhancing the adsorption into the skin of calcitonin and other bioactive peptides having a positive charge and substances similar to the same at a higher efficiency than in the past, and a treatment method using the same.

BACKGROUND ART

In the past, when administering bioactive peptides or bioactive proteins, oral administration resulted in a poor efficiency of absorption of the drug due to its breakdown by the digestive enzymes in the gastrointestinal tract and enzymes of the intestinal walls, breakdown by intestinal bacteria, absorption by food, etc., and therefore, the general practice had been for administration by injection. Administration by injection, however, is painful to patients and cannot, with some exceptions, be performed by themselves and therefore, a specialist had to be relied on. Therefore, development of a method of administration taking the place of injection has been desired. Active research on new drug delivery systems (DDS) is currently underway and energetic studies are being conducted on oral preparations, rectal preparations, nasal preparations, transdermal preparations, etc. in combination with absorption promoters, but nothing satisfactory has yet come out. In particular, development of new technology is being awaited in administration of hormone-like peptides for which time controlled or intermittent administration is required.

These bioactive peptides are difficult to be absorbed and hard to be absorbed in an effective dosage. Further, since they are amphipathic molecules, when present in an aqueous solution, they are adsorbed on various storage containers and, as a result, are hard to recover from the materials, which is extremely disadvantageous in a small amount of preparations. Accordingly, in the past, containers have been treated with silicone, protein with relatively low adsorption activities compared with these bioactive peptides have been made copresent, or surfactants, hydrocarbons, amino acids, etc. have been blended in so as to try to prevent adsorption on the storage containers (for example, see Japanese Laid-Open Patent Application (Kokai) No. 61-221125 and Japanese Laid-Open Patent Application (Kokai) No. 63-57527).

Iontophoresis is a system for promoting transdermal absorption using electricity. This method of treatment has been known since early 1900. Namely, the molecules having a positive charge pass through the skin layer from the anode side and the molecules having a negative charge pass from the cathode side in an electric field generated through the anode and cathode during conductance of power (J. Controlled Release 18, 213–220, 1992), but recently this technology has been reevaluated as a system for administration of bioactive peptides. Iontophoresis is known to improve the transdermal absorption of peptide type drugs. Much research is going on toward practical application. In iontophoresis, the smaller sized molecules of the peptide easily pass through the skin. Further, steps taken in the preparations to suppress association of the molecules raise the efficiency of permeation through the skin.

As an iontophoretic interface capable of serving as such a drug holding member, an interface having a water-soluble layer, for being impregnated with and holding an ionic liquid drug, comprising a paper material, fabric material, textile material, plastic foam or water-absorbing plastic or other sponge or porous material has been reported. An interface comprising a porous member made of a ceramic etc. or a non-electroconductive material having a porous or capillary construction has also been reported.

There has not, however, been obtained any iontophoretic interface comprising an iontophoretic interface coated with, adhered with, or impregnated with a bioactive peptide or, followed by drying in a solid or sub-dried state which is sufficient in terms of the amount of transdermal absorption and satisfactory in terms of the efficiency of utilization of the drug. The main reason is that these bioactive peptides cannot be used when adsorbed on the drug holding member. As a method to solve this problem, we have already reported a method which coats a non-electroconductive material having a porous or capillary construction with a high molecular weight protein to prevent the adsorption of the drug on the porous material and secure an extremely effective transdermal absorption in a small amount and which is superior in terms of safety as well (see Japanese Laid-Open Patent Application (Kokai) No. 6-16535). This method is extremely effective, but the coating agent used is high priced protein, for example, BSA (bovine serum albumin), which has problems with stability and is troublesome to store over long periods of time. Development of a better method is therefore being sought.

To prevent adsorption of the bioactive peptide on the equipment, as explained above, the method has been reported of adding to the drug-containing solution, for example, benzalkonium chloride or benzethonium chloride etc. in a range of concentration in the solution of 0.1 to 2.0%, but there is the problem with a transdermal drug delivery system using iontophoresis that the target drug ions and the copresent ions electrically compete and, as a result, the rate of transport in the permeation of the drug is lowered, which is a problem from the viewpoint of the objective of raising the efficiency of utilization.

Further, such bioactive peptides are problematic in that, when delivered by transdermal absorption, since the amount used is minute, the drug will be adsorbed at the surface of the skin where it is to be absorbed and accurate control of the dosage into the body will become difficult, and therefore, development of an effective method of preventing adsorption on the skin has been sought for a long time.

DISCLOSURE OF INVENTION

As explained above, in the past, there have been the problems that, in the techniques for transdermal delivery of a drug, bioactive peptide type drugs would irreversibly be adsorbed or be adsorbed in a difficult to redissolve manner on the surface of the skin resulting in inaccurate dosage. There was also a practical problem from the viewpoint of safety or in terms of economy when using peptides, which are priced expensively even in a small amount.

In view of this situation, the object of the present invention is to provide a technique for coating an iontophoretic interface which raises the efficiency of utilization of a bioactive peptide drug with a good reproducibility, is inexpensive, stable, and practical.

Other object of the present invention is to provide a technique for pretreatment of the skin for iontophoresis which raises the efficiency of utilization of the drug with a good reproducibility and which is inexpensive, stable, and practical by using a cationic surfactant having a sterilizing and disinfecting effect.

In accordance with the present invention, there is provided an iontophoretic interface comprising a drug holding member and a surface coating layer of an ionic surfactant formed on the surface of the drug holding member.

In accordance with the present invention, there is also provided a skin treatment composition for iontophoretic transdermal administration comprising, as a pretreatment agent for the portion of the skin to be treated, an aqueous solution containing a cationic surfactant or a disinfecting alcohol solution.

In accordance with the present invention, there is further provided a skin pretreatment method comprising pretreating a portion of a skin to be treated by an aqueous solution containing a cationic surfactant having a sterilizing and disinfecting effect or a disinfecting alcohol solution when administering a drug to a skin by iontophoretic transdermal delivery so as to coat the drug adsorbing portion of the skin surface and to improve the efficiency of permeation of the drug (or effective rate of use).

BRIEF DESCRIPTION OF DRAWINGS

The present invention will be explained in further detail below with reference to the drawings.

FIG. 3 is a graph of the test results obtained in Example 1;

FIG. 4 is a graph of Example 2 for explaining the present invention, wherein Group 1 in FIG. 4 shows the changes along with time of the concentration of calcitonin in a drug solution in the case of washing the skin with just distilled water, while Group 2 shows the changes along with time of the concentration of calcitonin in the drug solution in the case of washing the skin with an aqueous solution of 1% by weight of benzalkonium chloride; and FIG. 5 is a graph of Example 3 for explaining the effects of the present invention, wherein Group 3 of FIG. 5 shows the changes along with time of the concentration of calcium in the serum, when administering calcitonin by iontophoresis after wiping the skin clean with absorbent cotton containing 70% by weight of ethanol (serum Ca reducing effect) and Group 4 shows the changes along with time of the concentration of calcium in the serum when administering calcitonin by iontophoresis after wiping the skin clean with absorbent cotton containing 70% by weight of ethanol including 0.01% by weight of benzalkonium chloride (serum Ca reducing effect).

BEST MODE FOR CARRYING OUT THE INVENTION

Figure 1:
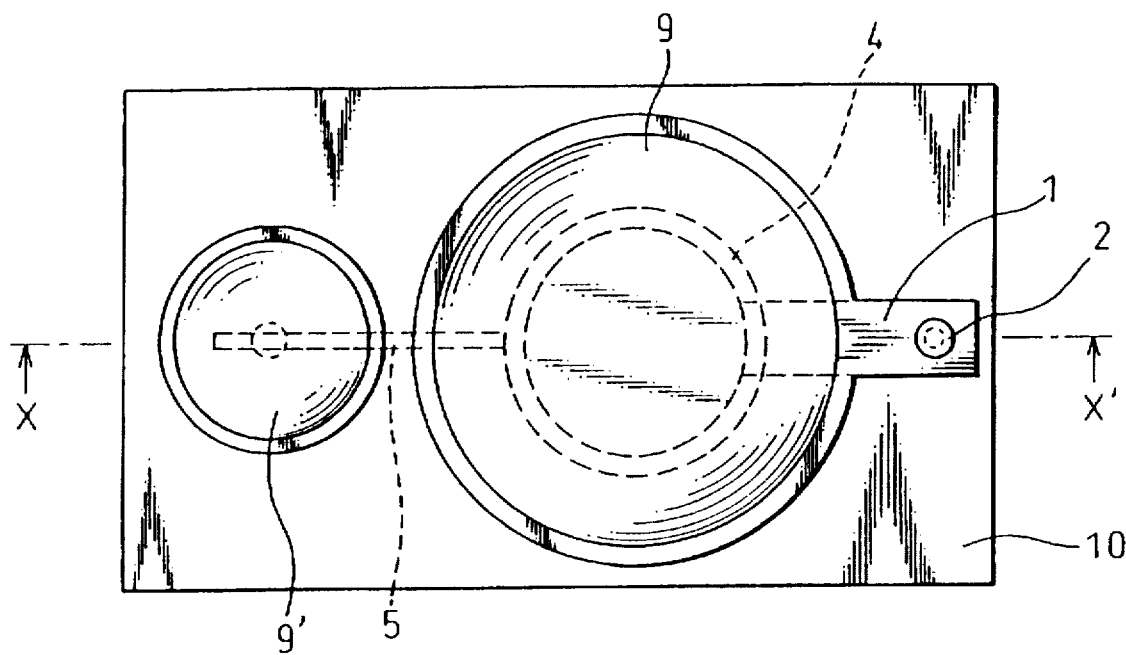
FIG. 1 is a plan view of the structure of an applicator device including the interface used in the Examples.

The present inventors engaged in intensive effort to solve the above problems and discovered that by coating a film of a disinfecting ionic surfactant on the surface of an iontophoretic interface device comprising a non-electroconductive material with a porous or capillary construction, the transdermal absorption of a drug is safely and remarkably improved without irritation to the skin and the efficiency of utilization of the drug is improved. We engaged in further intensive research and, as a result, completed the present invention.

That is, the present invention relates to an iontophoretic interface comprising a drug holding member formed with a coating layer of an ionic surfactant.

The above-mentioned drug holding member is a member coming into contact with a solid drug or liquid drug and comprises a non-electroconductive material with a porous or capillary construction. The above-mentioned ionic surfactant is characterized by being preserving and disinfecting. Specifically, it is characterized by being a drug additive such as benzalkonium chloride, benzethonium chloride, alkylbenzene sulfonate, etc. The ionic surfactant either does not elute into the liquid drug at the time of use or when eluting out does so in a range of concentration of 0.01% by weight or less. The above-mentioned drug is particularly preferably a bioactive peptide requiring improvement of the efficiency of drug utilization.

The drug used in the present invention is not particularly limited so long as it is a pharmaceutically effective bioactive peptide, but the following drugs may be mentioned, that is, calcitonin, an adrenocorticotropic hormone, parathyroid hormone, insulin, secretin, oxytocin, angiotensin, β-endorphins, glucagon, vasopressin, somatostatin, gastrin, luteinizing hormone releasing hormone, enkephalin, neurotensin, atrial sodium diuretic peptides, growth hormone, bradykinin, Substance P. dynorphin, thyroid-stimulating hormone, prolactin, interferon, interleukin, G-CSF, glutathione peroxidase, superoxide dismutase, desmopressin, somatomedin, melanophore stimulating hormone, muramyldipeptide, bonbessin, vasoactive intestinal peptide, cholecystokinin-8, calcitonin gene related peptide, endothelin, thyrotropin-releasing hormone, and derivatives of these bioactive peptides, etc. The amount of mixing of the bioactive peptide into the liquid composition of the present invention need only be an amount sufficient to exhibit the desired pharmaceutical effect. This differs depending on the type of the drug, the body weight of the patient, and the symptoms and may be suitably selected depending upon these conditions.

The present inventors further discovered that by wiping clean and coating the surface of the skin where the drug is to be administered by iontophoretic transdermal delivery in advance by an aqueous solution containing a cationic surfactant having a sterilizing and disinfecting effect or a disinfecting alcohol solution, the efficiency of safe utilization of the drug is remarkably raised, without causing irritation to the skin. They engaged in further studies to complete the present invention.

That is, according to the present invention, before administering a drug by iontophoretic transdermal delivery, the skin surface is wiped clean by an aqueous solution containing a cationic surfactant having a sterilizing or disinfecting effect so as to enable improvement of the efficiency of utilization of the drug. The cationic surfactant used is, for example, a drug additive comprising benzalkonium chloride, benzethonium chloride, etc. The concentration of the treatment solution is such that the cationic surfactant does not elute from the skin after the skin treatment at the time of use or even if eluting the concentration in the drug is 0.01% by weight or less. When the concentration eluting from the skin is high, absorbent cotton moistened with water is used to wipe the skin clean. By the above washing method, it is possible to raise the efficiency of utilization of bioactive peptides exhibiting high activity in a small amount, in particular, positively charged peptides (for example, calcitonins).

EXAMPLES

The present invention will now be further illustrated by, but is by no means limited to, the following Examples.

Figure 2:
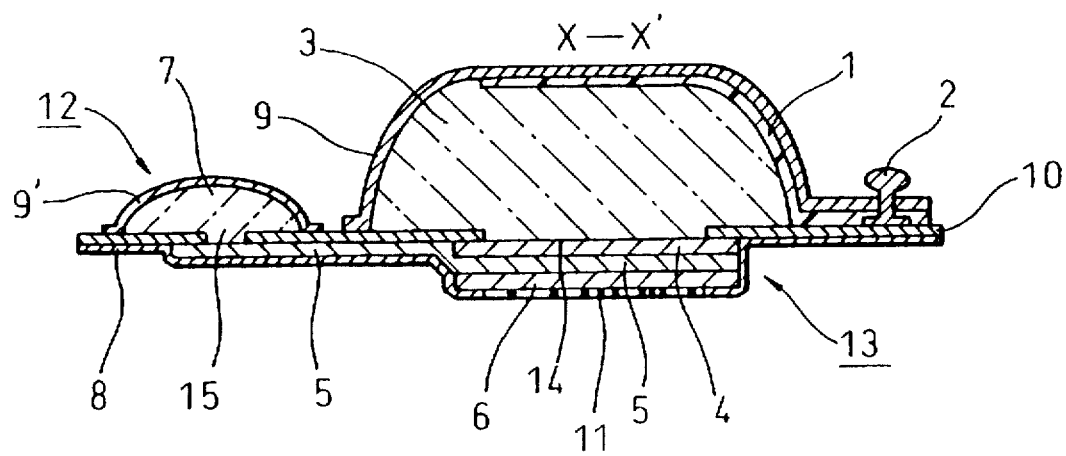
FIG. 2 is a cross-sectional view of the section X-X' of the structure in FIG. 1.

A preferable specific example of the iontophoretic interface of the present invention will be explained. The present invention is not particularly limited by this. In FIG. 1 and FIG. 2, two polyethylene cups (9) (9') are placed on top of a support (10) having pliability and hardness. In the cup (9') is stored a drug solution (7) comprising of distilled water for injection use (made by Fuso Yakuhin Kogyosha) etc. to form a reservoir (12). In the cup (9) is contained an electroconductive gel (3) composed of, for example, PVA water-containing gel containing NaCl. At the portion under the support (10) under the cup (9), a hole (14) formed so as to penetrate from the front to rear sides at use is made in the support (10). Further, an ion exchange membrane (4) (for example, AC-220 film (made by Asahi Chemical Industry Co., Ltd.)), nonwoven fabric (5) (for example, Bemberg® (made by Asahi Chemical Industry Co., Ltd.)), and a nylon porous member (6) (for example, Biodyne Plus® (made by Nihon Pall Ltd., Japan)) are arranged in a superposed form to form the applicator (13).

The nonwoven cloth (5) extends further under the support (10) to the portion positioned under the cup (9'). At the portion of the support (10) under the cup (9') where the nonwoven fabric (5) is positioned, a hole (15) is made which penetrates from the front to rear at the time of use.

These drug holding members, that is, the ion exchange membrane (4), nonwoven fabric (5), and nylon porous member (6) (in this case the holding including at least contact with a drug contact member also acceptable) are coated or impregnated uniformly by an aqueous solution of 0.01% benzalkonium chloride or else immersed in an aqueous solution of the same for treatment, then stripped of water and dried. Of the thus obtained AC-220 membrane, nonwoven fabric, and nylon porous member, the skin contact surface of the nylon porous member has deposited on it a bioactive peptide by a means such as spray coating or impregnation followed by drying for retention. The portion of the nylon porous member (6) coming into contact with the live skin has the drug (11) affixed to it. At the edges of the nylon porous member (6) and under the support (10) are for example disposed an adhesive tape (8) composed of Blenderm® (made by 3M Health Care Ltd.).

Example 1 (Test of Transdermal Drug Administration in Rats)

Method: Under pentobarbital anesthesia, 7 week old SD male rats had their stomach skin sheared by electric shears and shaved by a shaver, then absorbent cotton containing an aqueous solution of 70% by weight ethanol was used to lightly rub and disinfect the area. The interface or device shown in FIG. 1 and FIG. 2 was affixed so that the skin contact surface where calcitonin (synthetic salmon calcitonin made by Sigma Co.) was held dried in an amount of 2 IU (0.4 µg) per sheet of drug film was adhered to the stomach skin of the rat. The applicator (13) was used to supply water from the reservoir (12) just before use to redissolve the dried drug (11). Specifically, the water was supplied from the reservoir (12) through the opening (15) shown in FIG. 1 and the nonwoven fabric (5) having the capillary construction to reach the nylon porous member (6). Electric power was applied by a depolarization type constant voltage and high duty pulse of 6 V, 30 kHz, and 30% duty for 45 minutes. After a predetermined time, blood was sampled from the jugular vein. This was centrifugally separated at 12,000 rpm for 5 minutes and the supernatant used as the serum sample. The serum calcium was measured by the o-cresol phthalein complex method (Calcium C Test Wako made by Wako Pure Chemical Industries, Ltd.).

As clear from the test results of FIG. 3, when using a nylon porous film not coated with a surfactant (nontreated group), the reduction in the calcium value in the rat serum caused by the calcitonin was a maximum of approximately 17%, while when using a nylon porous film treated by benzalkonium chloride (treated group), the reduction in the calcium value in the rat serum caused by the calcitonin was a maximum of 28%, i.e., the pharmaceutical effect of the drug calcitonin was greater and a rise was shown in the efficiency of utilization of the drug.

Example 2 (Prevention Test of Skin Absorption of A Drug in Rats)

The stomach skin of male hairless rats of 13 weeks age were sheared by electric shears, then lightly rubbed and disinfected by absorbent cotton containing an aqueous solution of 70% ethanol. The skin was separated by scissors, then placed on a paper towel moistened with physiological saline with the epidermal side facing up. An acrylic chamber cup (18 mm diameter and 20 mm height) was immersed for 5 minutes in a silicone coating and an aqueous solution of 1% benzalkonium chloride, then was fully rinsed and washed by distilled water. The acrylic chamber cup was adhered to the skin by medicinal adhesive and dried, then filled with 2 ml of an aqueous solution of 1% benzalkonium chloride (Group 2)or distilled water as a control (Group 1) and allowed to stand for 5 minutes. The solution was removed then the cup was fully rinsed and washed by distilled water. As one example of the polypeptide drug, a solution of 2 µg/ml of calcitonin (synthetic salmon calcitonin made by Sigma Co.) in distilled water was prepared. A 2 ml amount each were added to two acrylic chamber cups treated as explained above which were then allowed to stand. Amounts of 100 µl each were sampled after 1, 2, and 6 hours and the amount of nonabsorbed calcitonin in the solution was measured by high pressure liquid chromatography.

As shown in FIG. 4, the amount of calcitonin in the aqueous solution in the acrylic chamber cup standing stationary on the skin after one hour was approximately 60% in the case of washing by 1% benzalkonium chloride in terms of the initially prepared concentration (Group 2) and approximately 30% in the case of cleaning the skin just by distilled water (Group 1). This was because of the calcitonin adsorbed on the skin of the rats. The amount of the calcitonin not absorbed from after 2 hours to after 6 hours was about 60 to 70% in the case of washing by 1% benzalkonium chloride and about 20 to 25% in the case of washing the skin with just distilled water, that is, an effect of preventing adsorption of calcitonin at the skin was observed in washing by benzalkonium chloride.

Example 3 (Test of Transdermal Iontophoretic Administration of A Drug Using Rats)

Under pentobarbital anesthesia, 7 week old male SD rats had their stomach skin sheared by electric shears and shaved by a shaver, then absorbent cotton containing an aqueous solution of 70% by weight ethanol (Group 3) or absorbent cotton containing an aqueous solution of 70% by weight ethanol plus 0.01% benzalkonium chloride (Group 4) was used to lightly rub and disinfect the areas. Calcitonin dried and held in an amount of 0.04 μg per sheet of drug film (synthetic salmon calcitonin made by Sigma Co.) was dissolved in an aqueous solution at the time of use and used for one rat. The conditions of conductance of power in the iontophoresis were a depolarization type constant voltage high duty pulse of 6 V, 30 kHz, and 30% duty applied for 45 minutes. The blood was sampled after a predetermined time from the jugular vein and was centrifugally separated at 12,000 rpm for 5 minutes. The supernatant was used as the serum sample. The calcium in the blood was measured by the o-cresol phthalein complex method (Calcium C Test Wako made by Wako Pure Chemical Industries, Ltd.).

As clear from the test results of FIG. 5, when cleaning the skin before use of iontophoresis by 70% ethanol alone (Group 3), the reduction in the calcium value in the rat serum due to the calcitonin is approximately 13% even at the maximum, while when cleaning by 70% by weight ethanol containing 0.01% benzalkonium chloride (Group 4), the reduction in the calcium value in rat serum due to calcitonin is a maximum of about 30% or larger than the pharmaceutical efficacy of drug calcitonin and showing a rise in the rate of drug utilization.

INDUSTRIAL APPLICABILITY

In this way, according to the present invention, it is possible to ensure effectiveness and safety in the transdermal administration of bioactive peptides by iontophoresis and possible to obtain a high bioavailability never achieved before in conventional iontophoresis. Accordingly, utilization can be expected in the medical field where suitability of the bioactive peptide drug for transdermal absorption is required.

We claim:

1. A device for iontophoretic transdermal drug delivery comprising a drug holding member adapted to contain a peptide drug, the drug holding member having a surface which is coated with an ionic surfactant present in such an amount that the surfactant is not eluted at more than 0.01% by weight of the total volume eluted during iontophoresis.

2. The device of claim 1, wherein said ionic surfactant is at least one surfactant selected from the group consisting of benzalkonium chloride, benzethonium chloride, and alkylbenzene sulfonate.

3. The device of claim 2, wherein at the time of use, said ionic surfactant either does not elute into the drug solution or elutes only at a concentration of 0.01% by weight or less.

4. A method of iontophoretic transdermal drug administration comprising as a first step wiping the portion of the skin to be used for drug administration with an aqueous solution containing a cationic surfactant, and as a second step applying the drug iontophoretically, wherein the concentration of the surfactant in the aqueous solution is such that, during iontophoretic transdermal drug administration, the cationic surfactant elutes from the skin at 0.01% by weight or less of the total volume eluted during iontophoresis.

5. A method of improving the efficiency of permeation of a drug during iontophoretic transdermal drug administration, the method comprising as a first step wiping a portion of the skin to be used for drug administration with an aqueous solution containing a cationic surfactant, and as a second step applying the drug iontophoretically, wherein the concentration of the surfactant in the solution is such that, during iontophoretic transdermal drug administration, the cationic surfactant elutes from the skin at 0.01% by weight or less as compared to the weight of the drug administered, the method further comprising wiping the skin with water after the first step when the concentration of the surfactant in the solution is such that elution from the skin of the surfactant during iontophoresis would be higher than 0.01%.

6. The method of claim 5, wherein the aqueous solution contains at least one cationic surfactant selected from the group consisting of benzalkonium chloride, benzethonium chloride, and alkylbenzene sulfonate.

7. The method of claim 4, wherein the drug is a bioactive peptide exhibiting a high activity in a small amount.

8. The method of claim 5, wherein the drug is a bioactive peptide exhibiting a high activity in a small amount.

9. The device of claim 1, wherein the drug holding member is formed from a dry porous member coated thereon with a surfactant, wherein the iontophoretic transdermal drug administration can be effectuated at the time of iontophoresis by supplying a solution from an external reservoir.

10. An iontophoretic interface which comprises a drug holding member containing a drug composition comprising a peptide drug and which is substantially free of surfactant, the drug holding member having a surface which is coated with an ionic surfactant in an amount such that the surfactant is not eluted during iontophoresis at more than 0.01% by weight of the total volume of drug composition or components thereof eluted during such iontophoresis.

11. A method of iontophoretic transdermal drug administration comprising:

pretreating skin to be used for iontophoresis by wiping it with an aqueous pretreatment solution containing a cationic surfactant;

eluting a peptide drug through the pretreated skin by means of an iontophoretic device comprising an interface having a drug holding member containing a drug composition comprising the peptide drug and substantially free of surfactant, the drug holding member having a surface which is coated with an ionic surfactant;

whereby the amount of surfactant in the pretreatment solution and coated onto the surface of the drug holding member of the iontophoretic device is selected so that the amount of surfactant eluted during iontophoresis is not more than 0.01% by weight of the total volume of drug composition or components thereof eluted during iontophoresis.

12. A method of iontophoretic transdermal drug administration comprising:

pretreating skin to be used for iontophoresis by wiping it with an aqueous pretreatment solution containing a cationic surfactant;

eluting a peptide drug through the pretreated skin by means of an iontophoretic device comprising a drug holding member containing a drug composition comprising the peptide drug and substantially free of surfactant;

whereby the amount of surfactant eluted during iontophoresis is not more than 0.01% by weight of the total volume of drug composition or components thereof eluted during iontophoresis.

* * * * *